United States Patent [19]

Elias

[11] Patent Number: 5,807,820
[45] Date of Patent: Sep. 15, 1998

[54] CYCLOSPORIN COMPOSITIONS FOR TOPICAL APPLICATION

[75] Inventor: Peter M. Elias, Muir Beach, Calif.

[73] Assignee: Novartis AG, Basel, Switzerland

[21] Appl. No.: 446,984

[22] Filed: May 22, 1995

Related U.S. Application Data

[63] Continuation of Ser. No. 138,561, Oct. 18, 1993, abandoned, which is a continuation of Ser. No. 856,133, Mar. 23, 1992, abandoned, which is a continuation of Ser. No. 743,846, Aug. 12, 1991, abandoned, which is a continuation of Ser. No. 350,952, May 11, 1989, abandoned.

[30] Foreign Application Priority Data

May 13, 1988 [GB] United Kingdom .................. 8811357
Oct. 21, 1988 [GB] United Kingdom .................. 8824779

[51] Int. Cl.$^6$ ..................... A61K 38/13; A61K 38/12; A61K 38/00
[52] U.S. Cl. ................. 514/11; 530/317; 530/321
[58] Field of Search .................. 514/11, 9; 530/317

[56] References Cited

U.S. PATENT DOCUMENTS

| | | | |
|---|---|---|---|
| 4,388,307 | 6/1983 | Cavanak | 514/11 |
| 4,639,434 | 1/1987 | Wenger et al. | 514/11 |
| 4,649,047 | 3/1987 | Kaswan | 514/11 |
| 4,798,823 | 1/1989 | Witzel | 514/11 |
| 4,839,342 | 6/1989 | Kaswan | 514/11 |
| 4,970,016 | 11/1990 | Horrobin | 510/221 |
| 4,970,076 | 11/1990 | Horrobin et al. | 424/456 |

FOREIGN PATENT DOCUMENTS

| | | |
|---|---|---|
| 43738 | 1/1982 | European Pat. Off. . |
| 127426 | 12/1984 | European Pat. Off. . |
| 255485 | 2/1988 | European Pat. Off. . |
| 271983 | 6/1988 | European Pat. Off. . |
| 300785 | 1/1989 | European Pat. Off. . |
| 3531597 | 3/1987 | Germany . |
| 97544 | 12/1985 | Japan . |
| 61-280435 | 4/1986 | Japan . |
| 249918 | 11/1986 | Japan . |
| 61280435 | 11/1986 | Japan . |
| 156038 | 1/1987 | Japan . |
| 1518683 | 7/1978 | United Kingdom . |
| 2142237 | 1/1985 | United Kingdom . |
| 2206119 | 12/1988 | United Kingdom . |
| 87/06463 | 11/1987 | WIPO . |

OTHER PUBLICATIONS

Kelley et al. Transplantation Proceedings, 21(1), 848–849, Jan. 1989.
Biren, et al., J. Invest. Dermatol., Abstract 17, p. 419 (1984).
Biren, et al., Arch. Derm., vol. 122, pp. 1028–1032 (1986).
Cole, et al., Contact Dermatitis, vol. 19, pp. 129–132 (1988).
Cooper, J. of Pharma. Sci. vol. 73, No. 8, pp. 1153–1156 (Aug. 1984).
Gilhar, et al., British Journal of Dermatology, vol. 119, pp. 767–770 (1988).
Gilhar, et al., Correspondence, vol. 18, No. 2, Part 1, pp. 378–379 (1988).
Golden, et al., Journal of Pharmaceutical Sciences, vol. 76, No. 1, pp 25–28 (Jan. 1987).
Pendry, et al., Cyclosporin A, Proc. Internat. Conference on Cyclosporin A, Cambridge, UK, Elsevier, pp. 77–81 (1982).
Schulze, et al., Acuta Sandoz, vol. 13, pp. 102–103 (1987).
Takada, et al., J. Pharmacobia–Dyn. vol. 8, pp. 320–323 (1985).
Takada, et al., Pharma. Research, vol. 3, No. 1, pp. 48–51 (1986).
Parodi et al., Arch. Derm., vol. 123, 165–166 (Feb. 1987).
Aldridge et al., Clin. Exp. Immunol., vol. 66, 582–589 (1986).
Kelley et al., Transpl. Proc., vol. 21, No. 1, 848–849 (Feb. 1989).

Primary Examiner—Cecilia J. Tsang
Assistant Examiner—Michael Berin
Attorney, Agent, or Firm—Gabriel Lopez

[57] ABSTRACT

Pharmaceutical compositions comprising a cyclosoporin, e.g. Ciclosporin, and a mono- or poly-unsaturated fatty acid or alcohol, e.g. oleic acid or oleyl alcohol. The compositions are suitable for dermal application, e.g. in the treatment of autoimmune disease of the skin or for the promotion of hair growth.

7 Claims, 1 Drawing Sheet

CYCLOSPORIN COMPOSITIONS FOR TOPICAL APPLICATION

This is a continuation of application Ser. No. 08/138,561, filed Oct. 18, 1993, which in turn is a continuation of application Ser. No. 07/856,133, filed Mar. 23, 1992, which in turn is a continuation of application Ser. No. 07/350,952, filed Aug. 12, 1993, which in turn is a continuation of application Ser. No. 07/350,952, filed May 11, 1989, all of which are now abandoned.

The present invention relates to novel galenic formulations comprising a cyclosporin as active ingredient, in particular to novel galenic formulations for topical application, more particularly for dermal application, especially for the treatment of dermatological disease, in particular dermatological disease involving morbid proliferation and/or keratinisation of epidermal cells.

The cyclosporins comprise a recognised class of pharmaceutically active, cyclic undecapeptides. The parent compound of this class is the known pharmaceutical agent cyclosporin A or Ciclosporin, commercially available under the Registered Trade Mark SANDIMMUN. Other cyclosporins include, for example (Dihydro-MeBmt)$^1$-(Val)$^2$-Cicloporin (also known as dihydro-cyclosporin D) and (Nva)$^2$-Ciclosporin (also known as cyclosporin G). Many further members belonging to the cyclosporin group are, for example, disclosed in: Traber et al., Helv. Chim. Acta, 60, 1247–1255 (1977), and Helv. Chim. Acta, 65, 1655–1667 (1982); Kobel et al., Europ. J. Applied Microbiology and Biotechnology 14, 273–240 (1982); von Wartburg et al., Progress in Allergy, 38, 28–45 (1986); Wenger, Transpl. Proc., 15, Supp. 1, 2230 (1983), Angew. Chem. Int. Ed., 24, 77 (1985) and Progress in the Chemistry of Organic Natural Products 50, 123 (1986); as well as e.g. U.S. Pat. Nos. 4,108,985, 4,210,581, 4,220,641, 4,288,431, 4,554,351, 4,396,542 and 4,798,823; European Patent Publications nos. 0 034 567, 0 056 782, 0 300 784 and 0 300 785, 0 296 122; UK Patent Specification No. 2 206 119, and International Patent Publication No. WO 86/02080.

As the parent of the class, Ciclosporin has so far received the most attention. The primary area of clinical investigation for Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Ciclosporin has achieved a remarkable success and reputation and is now widely employed in clinic.

At the same time, applicability of Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific auto-immune diseases for which Ciclosporin therapy has been proposed or applied include, autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Grave's disease, sarcoidosis, multiple sclerosis, primary billiary cirrhosis, primary juvenile diabetes (diabetes mellitus type I), uveitis (anterior and posterior), autoimmune conjunctivitis (including keratoconjunctivitis sicca and vernal keratoconjunctivitis), interstitial lung fibrosis, psoriatic arthritis and glomerulonephritis (with and without nephrotic syndrome, e.g. including idiopathic nephrotic syndrome or minimal change nephropathy).

Further areas of investigation have been potential applicability as an anti-parasitic, in particular anti-protozoal agent, with possible uses suggested including treatment of malaria, coccidiomycosis and schistosomiasis, use as a hair-growth stimulant, e.g. for the treatment of alopecia, and use in the treatment of multi-drug resistant tumors and the like.

Other cyclosporins exhibit comparable pharmacological utility as Ciclosporin and various proposals for their application, in particular in one or other of the above identified indications, are prevelant in the literature.

Despite the very major contribution which Ciclosporin has made, in particular in relation to the areas of organ transplant and the therapy of autoimmune diseases, an obvious impediment to wider application has been its reported side-reactions, e.g. nephrotoxic reactions, when administered enterally. Thus though Ciclosporin has already been shown to be of considerable potential value in the treatment of various diseases affecting, e.g. the skin, the risk of side-reaction following oral therapy presents a major barrier to therapy employing oral dosage forms.

To meet such difficulties it has been proposed that Ciclosporin should be applied topically rather than enterally. However attempts to provide topical Ciclosporin formulations providing effective treatment have hitherto failed or proved unsatisfactory for practical general usage or for usage in particular conditions. The present invention provides novel galenic products for topical, in particular dermal, administration, comprising a cyclosporin, e.g. Ciclosporin, as active ingredient, which meet difficulties hitherto encountered. In particular the invention provides novel galenic products, in particular for dermal administration, comprising a cyclosporin, e.g. Ciclosporin, as active ingredient and enabling treatment of diseases affecting the skin, for example diseases discussed in "Dermatological Applications of Cyclosporin", Brien et al., Arch. Dermatol., 122, 1028–1032 (1986), in particular autoimmune disease of the skin or diseases of the skin having an autoimmune aetiology or an aetiology comprising an autoimmune component. The galenic products of the invention are in particular applicable to treatment of dermatological disease, e.g. as aforesaid, involving morbid proliferation and/or keratinisation of the epidermis, especially to treatment of psoriasis, as well as dermatitides, including atopic dermatitis, contact dermatitis or allergic contact dermatitis. The products of the invention are also of use in the promotion of hair growth. e.g. for the treatment of alopecia including alopecia areata, alopecia universalis, male pattern alopecia or alopecia associated with other autoimmune or autoimmune-related disease such as psoriatic alopecia. Other uses for which the composition of the invention are indicated include the maintenance of skin grafts as well as e.g. the treatment of pemphigus (including pemphigus vulgaris and bullus pemphigoid), ichthyosis, lichen ruber planus, vitiligo and scleroderma.

In its broadest aspect the present invention provides:
  a) a pharmaceutical composition comprising:
    i) a cyclosporin, e.g. Ciclosporin, and
    ii) a $C_{12\text{-}24}$ mono- or poly-unsaturated fatty acid or alcohol.

Preferred components, (i) in the composition of the invention are (Nva)$^2$-Ciclosporin and, especially, Ciclosporin.

Preferred components (ii) are $C_{12-24}$ mono- or poly- enoic acids and alcohols, in particular $C_{12-24}$ mono-, di- or trienoic acids and alcohols, especially straight-chain acids and alcohols. The configuration at the double bond(s) in such acids and alcohols may be cis or trans. In the case of polyenoic acids and alcohols all double bonds present suitably have either the cis configuration or the trans configuration. Acids and alcohols wherein the configuration at each double bond is cis are of particular interest.

Compositions of the invention are primarily for topical, e.g. dermal application, e.g. for the treatment of diseases or conditions or for uses as set forth above.

Acids and alcohols (ii) may comprise from 12 to 24 carbon atoms. Preferably they comprise from 16 to 20 carbon atoms, more preferably they comprise 18 carbon atoms.

Examples of such acids and alcohols suitable for use in accordance with the present invention are:

a) Vaccenic acid and vaccenyl alcohol of formula $$CH_3-(CH_2)_5-CH=CH-(CH_2)_9-X$$
$$TRANS$$

b) Cis-vaccenic acid and cis-vaccenyl alcohol of formula $$CH_3-(CH_2)_5-CH=CH-(CH_2)_9-X$$
$$CIS$$

c) Linoleic acid or linoleyl alcohol of formula $$CH_3-(CH_2)_4-CH=CH-CH_2-CH=CH-(CH_2)_7-X$$
$$CIS \quad CIS$$

d) Linolenic acid or linolenyl alcohol of formula $$CH_3-(CH_2-CH=CH)_3-(CH_2)_7-X$$
$$CIS$$

e) Elaidic acid or elaidic alcohol of formula $$CH_3-(CH_2)_7-CH=CH-(CH_2)_7-X$$
$$TRANS$$

f) Oleic acid and oleyly alcohol of formula $$CH_3-(CH_2)_7-CH=CH-(CH_2)_7-X$$
$$CIS$$

g) Petroselinic acid and petroselinyl alcohol of formula $$CH_3-(CH_2)_{10}-CH=CH-(CH_2)_4-X$$
$$CIS$$

h) Erucic acid or erucyl alcohol of formula $$CH_3-(CH_2)_7-CH=CH-(CH_2)_{11}-X$$
$$CIS$$

i) Nervonic acid and nervonyl alcohol of formula $$CH_3-(CH_2)_7-CH=CH-(CH_2)_{13}-X$$
$$CIS$$

wherein X=—CO—OH or —CH$_2$—OH.

Alcohols as defined above are of particular interest. Use of oleic acid and oleyl alcohol, especially oleyl alcohol is, in particular, preferred.

Components (i) and (ii) will suitably be present in the compositions of the invention in a ratio of from 1:0.05 to 1:30 p.p.w. preferably from 1:0.1 to 1:30 p.p.w. More suitably they will be present in a ratio of from 1:0.5 to 1:25, preferably 1:1 to 1:20, e.g. ca. 1:1, 1:5, 1:10 or 1:20 p.p.w. [(i): (ii)].

Component (i) will suitably be present in the compositions of the invention in an amount of from 0.1 to 50%, e.g. from ca. 1.0 to 50% by weight based on the total weight of the composition. More suitably component (i) will be present in an amount of from 0.5 to 25%, e.g. from ca. 1.0 to 20% by weight based on the total weight of the composition. Most suitably component (i) will be present in an amount of from 0.5 to 10%, e.g. ca. 1.0, 2.0, 2.5, 5.0 or 10% by weight based on the total weight of the composition.

Component (ii) will suitably be present in the compositions of the invention in an amount of from 1 to 90%, preferably from 2 to 30%, more preferably from 3 to 15% by weight based on the total weight of the composition. More suitably component (ii) will be present in an amount of from 3 to 12%, e.g. ca. 10% by weight based on the total weight of the composition.

The compositions of the invention will suitably comprise one or more carriers or diluents and/or other ingredients providing a carrier system for components (i) and (ii), e.g. thickening agents, emulsifying agents, preserving agents, moisturising agents, colourants and so forth.

Compositions in accordance with the invention may be in any form suitable for topical application, e.g. application to the skin surface, for example flowable, e.g. liquid or semi-liquid form, in the form of a powder or in the form of a topically applicable spray. Examples of suitable flowable forms include e.g. gels, including oil-in-water and water-in-oil emulsions, creams, pastes and ointments and the like as well as lotions, and tinctures, etc.

Selection of excipients for the preparation of such formulations will, of course, be determined by the particular condition to be treated, the status of the condition, area to be treated, skin condition and effect desired. Thus chronic psoritic plaques will more suitably be treated with hydrophobic, e.g. fat-based compositions, for example compositions in accordance with the invention comprising a petrolatum based ointment or cream as carrier medium. In contrast, compositions for use in the treatment of disease conditions involving acute phase inflammatory processes will more appropriately be treated with more hydrophilic compositions, e.g. compositions in accordance with the invention in the form of an oil-in-water emulsion or gel. Although, as explained in more detail below, compositions in accordance with the invention may comprise e.g. lower alkanols as e.g. diluent or diluent component, for example ethanol, use of these will preferably be avoided, e.g. where compromised skin is to be treated, as in the case of psoriasis.

Suitable further components for use in the preparation of compositions in accordance with the present invention are set forth under (iii) through (ix) below. Appropriate amounts of components listed are indicated in brackets, all amounts indicated being in percent by weight, based on the total weight of the composition (represented as "% b.w.c.")

(iii) As carrier vehicle components:

(iii)¹ Hydrocarbons, for example petroleum jellies, e.g. petrolatum or Vaseline$^R$, ceresin and solid paraffin and waxes including animal, vegetable and synthetic waxes such as for example, spermaceti, carnauba and bees wax, (5–70% b.w.c.);

(iii)² Hydrocolloid thickening agents capable of providing aqueous emulsions in gel, paste, cream or like form on combination with water, for example: gum arabic and traganth, alginic acids, altapulgite, colloidal silica, celluloses and cellulose derivatives such as hydroxypropylmethyl celluloses, methyl celluloses and sodiumcarboxymethyl celluloses, as well as other hydrocolloid polymeric materials, for example, polyvinyl resins, such as polyvinylacetates and polyvinylalcohols and polyacrylate or polymethacrylate resins, (0.5–30% b.w.c.)

(iii)³ Pharmaceutical grade water, e.g. in conjunction with (iii)² (5–80% b.w.c.)

(iii)⁴ Polyethleneglycols, e.g. PEG 400 or PEG 4000 (5–70% b.w.c.)

(iv) Fatty components serving as emollients or consistency promoters, for example: liquid hydrocarbons, e.g. liquid paraffins, fatty acid esters and waxes such as isopropylmyristate and cetylpalmitate, vegetable oils such as olive oils, corn oils and kernel oils and vegetable oil derivatives including e.g. hydrogenated vegetable oils and vegetable oil partial, e.g. mono- and di-, glycerides (1–70% b.w.c.)

(v) Surfactants as emulsifying or wetting agents for example:

Reaction products of natural or hydrogenated vegetable, e.g. castor, oils, and ethylene oxide, such as available under the trade name Cremophor, for example the products Cremophor RH 40, Cremophore RH60 and Cremophore EL. Also suitable for use in this category are the various tensides available under the trade name Nikkol, e.g. Nikkol HCO-60;

Polyoxyethylene-sorbitan-fatty acid esters e.g. of the type known and commercially available under the trade name Tween including the products Tween 20 [polyoxyethylene(20)sorbitanmonolaurate],
40 [polyoxyethylene(20)sorbitanmonopalmitate],
60 [polyoxyethylene(20)sorbitanmonostearate],
65 [polyoxyethylene(20)sorbitantristearate],
85 [polyoxyethylene(20)sorbitantrioleate],
21 [polyoxyethylene(4)sorbitanmonolaurate],
61 [polyoxyethylene(4)sorbitanmonostearate], and
81 [polyoxyethylene(5)sorbitanmonooleate];

Polyoxyethylene fatty acid esters and ethers, for example polyoxyethylene stearic acid esters of the type known and commercially available under the trade name Myrij, polyoxyethylene fatty acid esters known and commercially available under the trade name Cetiol HE and polyoxyethylene fatty acid ethers as known under the trade name Brij; and Polyoxyethylene-polyoxypropylene co-polymers, e.g. of the the type and commercially available under the trade names Pluronic and Emkalyx;

(2–50% b.w.c.)

(vi) Anti-microbial agents such as: methylparaben and propylparaben (0.1–0.2% b.w.c.); benzyl alcohol (1.0–2.0% b.w.c.); benzalconium chloride (0.002–0.02% b.w.c.); benzoic acid (0.1–0.15% b.w.c.); or sorbic acid (0.1–0.15% b.w.c.);

(vii) Anti-oxidants such as: t-butylhydroxytoluene (0.001–0.02% b.w.c.), α-tocopherol (0.001–5% b.w.c.), ascorbyl palmitate (0.001–1.0% b.w.c.), or propylgallate (0.001–0.02% b.w.c.);

(viii) Alkanols [other than as defined under (ii) above] including: lower alkanols, e.g. $C_{1-8}$-, preferably $C_{1-5}$-, alkanols, including mono- and poly-ols, e.g. as aqueous phase components of creams; and higher alkanols, e.g. comprising at least 8-carbon atoms, for example $C_{8-22}$ saturated mono- or poly-ols, especially $C_{16-18}$ saturated mono- or poly-ols, e.g. as thickeners or emulsifying agents.

Examples of suitable components (viii) include e.g. ethanol, n- and i-propanol (10–70% b.w.c.); 1,2-propylene glycol, ethylene glycol and glycerol (2–30% b.w.c.); and tetradecanol, octyl-, decyl-, lauryl-, myristyl-, cetyl- or stearyl-alcohol, 2-octyl-dodecanol and cholesterol (2–25% b.w.c.);

(x) Stabilizers such as microcrystalline starch, sodium-EDTA and magnesium sulfate (0.1–10% b.w.c.).

Compositions in accordance with the invention, e.g. as described above, will suitably be applied to the site of treatment, e.g. of atopic or contact dermatitic reaction, of psoriatic lesion or of hair loss, at regular intervals, e.g. once, twice or three times per day.

The term "pharmaceutical composition" as used herein is to be understood as embracing systems or devices comprising components (i) and (ii) and, suitably, one or more of (iii) to (ix) and allowing for or adapted to permit topical application of (i) in the presence of (ii). Such systems may, for example, include e.g. dermally applicable patches, plasters, cataplasms or the like in which the defined components are present in either physical or functional association. Such systems or devices thus include, for example, bi- or multi-layer or bi- or multi-phase patch or plaster systems in which, e.g. components (i) and (ii) are initially present apart or substantially apart, for example in a first and second layer or phase, and which allow for passage of the two components together or in association to the skin surface when applied dermally. Such systems may include any of those known or described in the art, e.g. for dermal application of pharmaceutical agents.

It will of course be understood that components chosen for use in the compositions, (or systems or devices) of the invention will be components which are acceptable for topical, e.g. dermal application.

Figure 1:
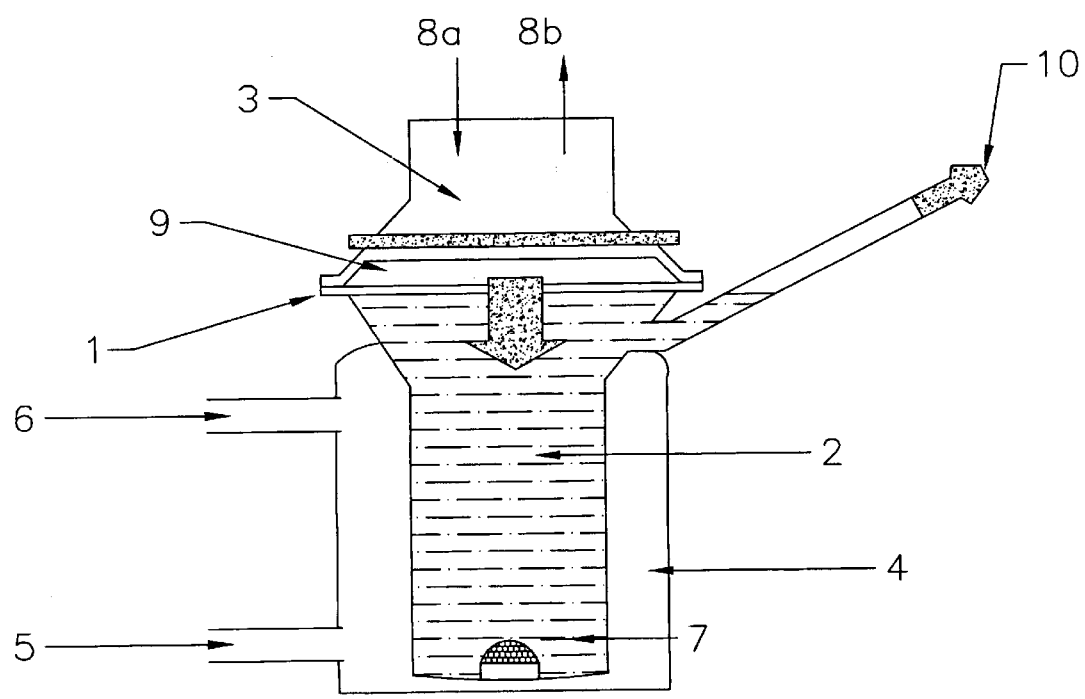
FIG. 1 is an elevational view of the apparatus used in Example 8.

The following examples are illustrative of the present invention.

EXAMPLE 1

Compositions in accordance with the invention suitable for dermal application, e.g. in the treatment of dermatitides or for the stimulation of hair growth.

| INGREDIENTS | % BY WEIGHT |
|---|---|
| 1.1. | |
| (i) CICLOSPORIN | 20 |
| (ii) VACCENYL ALCOHOL | 20 |

-continued

| | INGREDIENTS | % BY WEIGHT |
|---|---|---|
| (viii) | ISOPROPANOL | 40 |
| (v) | TWEEN 80. | 20 |
| 1.2. | | |
| (i) | CICLOSPORIN | 20 |
| (ii) | VACCENYL ALCOHOL | 16 |
| (viii) | 1,2 PROPELENE GLYCOL | 64 |

The components are intimately admixed in conventional manner and optionally combined with a thickening agent, for example, colloidal $SiO_2$ to provide a gel suitable for topical application. The amount of $SiO_2$ employed is suitably of the order of from 5 to 10% e.g. ca. 7% by weight based on the total weight of the final composition.

EXAMPLE 2

Liquid compositions in accordance with the present invention, suitable for the treatment of dermatitides or for stimulating hair growth, are prepared by admixture of 20% by weight CICLOSPORIN as component (i) 64% by weight of isopropanol as component (viii) and 16% by weight of each of the following acids/alcohols as component (ii):

| EXAMPLE | ACID/ALCOHOL |
|---|---|
| 2.1 | Vaccenyl alcohol |
| 2.2 | Oleic acid |
| 2.3 | Erucyl alcohol |
| 2.4 | Erucic acid |
| 2.5 | Petroselinyl alcohol |
| 2.6 | Nervonic acid |
| 2.7 | Linolenic acid |
| 2.8 | Linolenyl alcohol |
| 2.9 | Linoleyl alcohol |
| 2.10 | Cis-vaccenic acid |
| 2.11 | Vaccenic acid |
| 2.12 | Oleyl alcohol |
| 2.13 | Elaidic acid |
| 2.14 | Petroselinic acid |

For application the above compositions are suitably additionally combined with a thickener, e.g. as described under (iii) above, to provide an ointment cream or jelly, thus improving retention characteristics at the site of treatment.

EXAMPLE 3

Composition in accordance with the invention in the form of an oil-in-water emulsion (emulsion-gel with thickened water phase) suitable for the treatment of e.g. psoriatic lesion or dermatitides or for use in hair growth stimulation.

| | INGREDIENTS | % BY WEIGHT |
|---|---|---|
| (i) | Ciclosporin | 1.0 |
| (ii) | Oleylalcohol | 20.0 |
| (iii) | Carbopol 934 | 0.5 |
| | Sodium-hydroxide (neutralizer for carbopol) | 0.025 |
| | Pharmaceutical grade water | 52.455 |
| (iv) | Cetylpalmitate | 15.0 |
| (v) | Tween 80 | 10.0 |
| (vi) | Benzylalcohol | 1.0 |
| (vii) | Buthylhydroxytoluene | 0.02 |

(i) is dissolved in (ii) and (iv). (v) and (vii) are added and the mixture warmed to obtain a clear solution. (vi) is dissolved in ca. half of the water component of (iii) and warmed to about 70° C., combined with the previously recited ingredients using an homogenizer and cooled to about 40° C. The Carbopol component of (iii) is dispersed in about 20% of the water (iii), the homogeneous dispersion added to the previously obtained emulsion and again homogenized. Finally sodium-hydroxide is dissolved in the remaining water and added with careful stirring to thicken the emulsion thus yielding an emulsion gel.

EXAMPLE 4

Composition in accordance with the invention in the form of a cream, suitable for the treatment of psoriatic lesion, of dermatitides or for use in hair growth stimulation:

| | INGREDIENTS | % BY WEIGHT |
|---|---|---|
| (i) | Ciclosporin | 1.0 |
| (ii) | Oleyl alcohol | 10.0 |
| (iii) | Pharmaceutical grade water | 57.9 |
| (iv) | Miglyol 812 | 10.0 |
| (v) | Tween 60 | 8.0 |
| | Arlacel 60 | 2.0 |
| (vi) | Benzylalcohol | 1.0 |
| (vii) | Butylhydroxytoluene | 0.02 |
| (viii) | Cetylalcohol | 5.0 |
| | Stearylalcohol | 5.0 |

(vi) and (iii) are mixed and warmed to 70° C. The remaining ingredients are combined separately and warmed to 70° C. and then combined with (vi)+(iii) and homogenised to provide an emulsion. The obtained emulsion is cooled with stirring to provide a product cream.

EXAMPLE 5

Composition in accordance with the invention in the form of a fatty ointment, suitable for the treatment of psoriatic lesion or dermatitides or for the use in hair growth stimulation:

| | | |
|---|---|---|
| (i) | Ciclosporin | 1.0 |
| (ii) | Oleyly alcohol | 10.0 |
| (iii) | White petrolatum | 42.0 |
| (iv) | Liquid paraffin | 35.0 |
| (v) | Glycerolmonostearate | 12.0 |

(i) is dissolved in (ii). The remaining ingredients are combined and warmed to provide a clear solution to which (i)+(ii) are then added with stirring. The combined mix is cooled to provide an ointment.

EXAMPLE 6

Example 3 is repeated with substitution of each of the alcohols 2.1 to 2.14 of example 2, and examples 4 and 5 are repeated with substitution of each of the acids/alcohols 2.1 to 2.14 of example 2 for oleyly alcohol as component (ii) in the same or equivalent amount.

EXAMPLE 7

Examples 1 to 6 are repeated with substitution of [Nva]$^2$-Ciclosporin for Ciclosporin as component (i) in the same amount.

EXAMPLE 8

The experimental arrangement is shown in FIG. 1 attached. Skin used is hairless rat skin. The skin sample (1)

is mounted between the cell body (2), which serves as a receptor compartment and the cell cap (3), which serves as donor compartment. The cell body/receptor compartment (2) is charged with saline/20% methanol as receptor medium. This is maintained at 37° C. by surrounding water jacket (4), fed by water inlets and outlets (5) and (6) respectively, and stirred by means of star-head magnet (7). Cap (3) allows the passage of air as indicated by arrows (8a) and (8b), whereby test composition comprising tritated Ciclosporin ("$H^3$-SIM") is able to pass to the skin surface at (9). Samples from the receptor fluid are removable at sampling port (10).

The system is run for each test composition for 48 hrs. At the end of this time the system is disconnected, formulations are wiped off and the treated skin (2cm$^2$) removed from surrounding clamped skin by punching out. The stratum corneum is stripped away with Tesa-film. Stripping is done in a validated procedure 15 times, collecting 5 strips each into one vial labelled "stripping 1,2,3" respectively. The strips and the skin tissue consisting of epidermis and dermis are extracted with isopropanol and the amount of $H^3$-SIM in the extraction fluids determined. The amount of $H^3$-SIM in the receptor fluid of the diffusion cells is determined after both 24 hrs. and 48 hrs.

The following test compositions are employed (Ciclosporin component in all cases comprises $H^3$-SIM):

A. Comparative compositions (percentages by weight)

A.1. 20% Ciclosporin+80% ethanol.

A.2. 20% Ciclosporin+80% ethanol/azone (95:5 p.p.w.)

A.3. 20% Ciclosporin+80% ethanol/DMSO (70:30 p.p.w.)

A.4. Conventional Ciclosporin "drink-solution" as available under the Registered Trade Mark SANDIMMUN and comprising 10% Ciclosporin.

B. Compositions in accordance with the present invention

B.1. Composition of example 1.1

B.2. Composition of example 1.2

[NOTE: Compositions A.2 and A.3 comprise conventional skin-penetration enhancers azone and DMSO (dimethyl sulfoxide). SANDIMMUN drink-solution has been applied topically by various investigators in the attempted treatment of psoriasis. Compositions B.1 and B.2 are employed without thickener.]

The following quantities of $H^3$-SIM are recorded in the described test-apparatus.

| COMPO-SITION | Strip. 1 (μg) | Strip. 2 (μg) | Strip. 3 (μg) | Epidermis/ Dermis (μg) | Receptor medium 24 h (μg) | Receptor medium 48 h (μg) |
|---|---|---|---|---|---|---|
| A1 | 1349 | 20 | 25 | 113.0 | 32.0 | 60.6 |
| A2 | 408 | 15 | 4 | 38.8 | 2.3 | 3.1 |
| A3 | 1064 | 27 | 8 | 37.9 | 14.0 | 14.2 |
| A4 | 67 | 0 | 0 | 10.0 | — | 51.0 |
| B1 | 353 | 44 | 43 | 440.6 | 40.9 | 106.3 |
| B2 | 2237 | 459 | 57 | 942.6 | 47.3 | 45.1 |

Expressed as % of total cyclosporin applied for each composition these results may be presented as follows:

| COMPO-SITION | Strip.1 | Strip.2 | Strip.3 | Epidermis/ Dermis | Receptor medium 24 h | Receptor medium 48 h |
|---|---|---|---|---|---|---|
| A1 | 1.7% | 0.03% | 0.03% | 0.14% | 0.04% | 0.07% |
| A2 | 0.5% | 0.02% | 0.006% | 0.05% | 0.003% | 0.003% |
| A3 | 1.3% | 0.03% | 0.01% | 0.05% | 0.02% | 0.02% |
| A4 | 0.08% | — | — | 0.01% | — | 0.06% |
| B1 | 0.4% | 0.06% | 0.05% | 0.55% | 0.05% | 0.13% |
| B2 | 2.8% | 0.6% | 0.07% | 1.2% | 0.06% | 0.06% |

Compositions B.1 and B.2 in accordance with the invention thus exhibit markedly and surprisingly improved delivery through the cornea and, specifically, to the skin, than any of compositions A.1 to A.4. In the case of composition A.4, penetration through the cornea is achieved but the greater portion of the Ciclosporin delivered is subsequently lost from the skin to the medium in the receptor compartment.

Comparable results are obtainable employing other cyclosporins e.g. [Nva]$^2$-Ciclosporin.

EXAMPLE 9

The procedures of example 7 are repeated except that the strips and remaining skin tissue are shaken with scintillation cocktail (Quickszint 454) for 16 hrs. The amount of $H^3$-SIM in the extraction fluids is then determined. Amounts of $H^3$-SIM in the receptor fluid and diffusion cells is again determined after 24 and 48 hrs.

Compositions employed are those of examples 2.1 through 2.14 (without thickener) and comparative compositions A.1 and A.4 of example 7.

Each composition is applied to 3 penetration cells. The following results, being the mean of three determinations, are obtained.

| COMPO-SITION | Amount of Ciclosporin appl. (μg/cm$^2$) | Strip. 1 (μg) | Strip. 2 (μg) | Strip. 3 (μg) | Epidermis/ Dermis (μg) | Receptor medium 24 h (μg) | Receptor medium 48 h (μg) |
|---|---|---|---|---|---|---|---|
| A.1 | 47.5 mg | 673.9 | 12.8 | 11.4 | 52.5 | 4.0 | 14.2 |
| A.4 | 14.92 mg | 313.0 | 30.9 | 5.7 | 38.5 | 13.1 | 18.5 |
| 2.1 | 15.3 mg | 97.6 | 21.1 | 19.2 | 128.0 | 44.7 | 53.4 |
| 2.2 | 16.0 mg | 40.1 | 12.5 | 8.6 | 83.0 | 29.1 | 36.9 |
| 2.3 | 22.3 mg | 131.4 | 15.0 | 11.5 | 113.0 | 29.3 | 46.1 |
| 2.4 | 22.5 mg | 75.3 | 15.5 | 7.6 | 87.6 | 20.8 | 47.3 |
| 2.5 | 16.2 mg | 292.2 | 39.0 | 15.3 | 117.3 | 29.6 | 49.3 |
| 2.6 | 17.0 mg | 1536.5 | 21.5 | 1.6 | 37.0 | 29.5 | 50.9 |
| 2.7 | 19.3 mg | 117.0 | 37.1 | 15.2 | 54.7 | 31.5 | 39.9 |
| 2.8 | 19.9 mg | 61.1 | 18.2 | 9.2 | 171.4 | 75.2 | 72.0 |
| 2.9 | 17.0 mg | 324.7 | 56.2 | 23.8 | 132.7 | 19.6 | 32.3 |
| 2.10 | 17.6 mg | 621.0 | 24.5 | 5.8 | 69.7 | 17.6 | 27.9 |
| 2.11 | 17.1 mg | 5.5 | 18.3 | 5.5 | 58.8 | 18.3 | 25.1 |
| 2.12 | 15.2 mg | 252.9 | 15.8 | 12.2 | 109.5 | 38.2 | 47.1 |
| 2.13 | 15.4 mg | 1587.0 | 95.9 | 6.0 | 53.3 | 25.3 | 29.2 |
| 2.14 | 12.78 mg | 338.8 | 31.5 | 9.7 | 68.8 | 18.3 | 29.3 |

The obtained results indicate improved delivery for Ciclosporin, in particular long term delivery, into and through the skin, e.g. into the dermis/epidermis, than either of the comparative compositions A1 and A4. Comparable results are obtainable employing other cyclosporins, e.g. [Nva]$^2$-Ciclosporin.

EXAMPLE 10

In vivo skin penetration in the hairless rat.

The trials are carried out employing hairless rats as test animal. 40 μl test composition is applied to individual sites of area 6.15 cm² defined within plastic rings held in place with Leukoplast$^R$ and then wrapped with a Hustelatsts$^R$ band. Application is at 2 sites per animal and three animals are employed/test composition.

Blood samples are taken 24 hrs after commencement of the trial and the test animals are then sacrificed and skin biopsies isolated by punching. For this purpose a large area of skin including the application site is excised, pinned out on a cork board and covered with an aluminium foil A first 7.5 mm biopsy is taken (biopsy with fat).

In a second step the skin sample is transferred with the application side downwards onto a fresh aluminium foil and fatty tissue is removed with a scalpel. After transferring the skin with the dermis side onto a further alumunium foil, unstripped and stripped biopsies are taken. To calculate the total amount of penetrated and non-penetrated active agent, the aluminium foils are also extracted using ethyl-acetate/methanol (9:1).

Collected samples are pre-purified over Superclean$^R$ 3 ml LC-CN cartriges, Cyclosporin containing fractions subjected to HPLC and cyclosporin assayed by UV detection. (Detection limit in ca. 30–60 mg punch biopsies=ca.

50 ng/biopsy. Regression functions within the required range run linearly (0.1–30 mg/sample).

The following test compositions are employed:

| Composition I (Control) | |
|---|---|
| 5% by wt. | Ciclosporin |
| 95% by wt. | Isopropanol |
| Composition II | |
| 10% by wt. | Ciclosporin |
| 72% by wt. | Isopropanol |
| 18% by wt. | Oleic acid |
| Composition III | |
| 10% by wt. | Ciclosporin |
| 70% by wt. | Miglyol |
| 20% by wt. | Oleyl alcohol |
| Composition IV | |
| 5% by wt. | Ciclosporin |
| 74% by wt. | Miglyol |
| 21% by wt. | Oleyl alcohol |

The following results are obtained:

| | CICLOSPORIN CONCENTRATION | | | | |
|---|---|---|---|---|---|
| Composition | ng/ml/in blood at 24 hrs | Skin mg/g | | | |
| | | STRIPPED | %* | UNSTRIPPED | FAT |
| I | N | 0.065 (±0.045) | 1.5 | 4.47 (±0.71) | N |
| II | 0.041 (±0.013) | 0.27 (±0.063) | 9.7 | 2.78 (±0.792) | N |
| III | 0.067 (±0.009) | 0.178 (±0.031) | 46.0 | 0.39 (±0.092) | N |
| IV | 0.041 (±0.003) | 0.123 (±0.029) | 63.0 | 0.196 (±0.0032) | 0.007 (±0.009) |

*= % Ciclosporin in stripped skin without fat.
N = not determined.

Results show increased penetration for compositions comprising a component (ii) in accordance with the invention, in particular where oleyl alcohol is used as (ii).

EXAMPLE 11

CLINICAL TRIAL

The trial is conducted employing a group of volunteers (mixed male and female of average body weight) identified as exhibiting psoriasis. Subjects selected are primarily selected from long-term psoriasis sufferers and non-responders to conventional psoriasis therapy.

Each subject receives composition in accordance with the invention, e.g. composition in accordance with Example 3,4 or 5. Compositions are applied topically to a site of psoriatic lesion in an amount of from about 0.005 to about 0.05 g/cm². Application is effected 1,2 or 3× daily depending on the extent of lesion. Treatment is continued for each subject for a total period of at least 2 weeks. Alternative psoriasis treatment is withdrawn prior to and during topical Ciclosporin treatment.

Each subject undergoes full dermatological examination prior to commencement of Ciclosporin treatment to determine extent, location and severity of psoriatic lesions. Each subject is also questioned to determine subjective experience of the disease. Examination is repeated at weekly intervals and again at the conclusion of treatment and all changes in condition are noted. At the conclusion of treatment each subject is again questioned to determine subjective experience of the disease. All changes in the subjects' condition, especially extent, intensity of lesion (erythema, infiltration, desquamation) as well as any side effects, are noted. Results obtained on administration of composition in accordance with the invention are compared with those obtained for a control group receiving a placebo composition not comprising Ciclosporin. Results obtained show marked reduction of psoriasis and, in particular, improvement of epidermal lesion in subjects receiving composition in accordance with the invention administered as described as compared with control groups receiving placebo. Compositions in accordance with the invention tested are found to be well tolerated.

Efficacy of the compositions of the invention may also be demonstrated in trials employing subjects exhibiting atopic dermatitides or requiring treatment for alopecia, e.g. employing any of the compositions of examples 1 to 5.

Equivalent results are obtainable employing compositions in accordance with examples 6 and 7.

Amounts of composition in accordance with the invention, as well as rate of application required for effective therapy will of course vary depending, e.g. on the condition to be treated, the extent and severity of affliction, the effect desired and the concentration of components in the composition employed in particular of component (i). In general however satifactory results e.g. in the treatment of dermatitides, alopecia or psoriasis, will be obtained on administration e.g. of topically applied creams, gels, lotions, tinctures or the like comprising ca. 1 t 10% component (i) in amount of from ca. 0.005 to ca. 0.05 g/cm², 1, 2, or 3× daily. In a further series of embodiments the present invention also provides.

b) A pharmaceutical composition comprising a component (i) and a component (ii) as hereinbefore defined, component (ii) being present in said composition in a concentration sufficient to enhance or enable dermal penetration of component (i);

c) A pharmaceutical composition comprising a component (i) and a component (ii) as hereinbefore defined, the concentrations and relative proportions of components (i) and (ii) providing dermal delivery of component (i) in an immunosuppressively effective amount or amount effective for the stimulation of hair growth via topical administration of the defined composition;

d) A method of treating disease, e.g. autoimmune disease, of the skin, for example psoriasis or dermatitides, e.g. of any type as hereinbefore set forth, or of stimulating hair growth, for example for the treatment of alopecia, e.g. of any type as hereinbefore set forth, in a subject in need thereof, which method comprises topical application, e.g. application to the skin, of an effective amount of a composition as hereinbefore defined, e.g. as defined under any one of (a) to (d) above; and e) A pharmaceutical composition as hereinbefore defined, e.g. as defined under any of (a) to (c) above, for use in a method as set forth under (d) above.

I claim:

1. A topical pharmaceutical composition for dermal administration comprising, based on total weight,:
   (i) from 0.1 to 50% of a cyclosporin,
   (ii) from 1 to 90% of a $C_{12-24}$ mono- or poly-unsaturated fatty alcohol, wherein the weight ratio of the components (i):(ii) is from 1:0.05 to 1:30, and
   (iii) one or more pharmaceutically and dermally acceptable topical carriers or diluents therefor.

2. A composition of claim 1 wherein the cyclosporin is cyclosporin A.

3. A composition of claim 1 wherein component (ii) is selected from the group consisting of trans-vaccenyl-, cis-vaccenyl-, linoleyl-, linolenyl-, elaidic-, oleyl-, petroselinyl-, erucyl-, and nervonyl-alcohol.

4. A composition of claim 3 wherein component (ii) is oleyl alcohol.

5. A composition of claim 1 further comprising isopropanol, propylene glycol, ethanol, ethylene glycol, glycerol, tetradecanol, octyl-, decyl-, lauryl-, myristyl-, cetyl- or stearyl-alcohol, 2-octyl dodecanol, or cholesterol.

6. A composition of claim 1 comprising from 1.0 to 20% of a cyclosporin.

7. A gel, emulsion, paste, or lotion comprising a pharmaceutical composition of claim 1.

* * * * *